United States Patent [19]
Chen

[11] Patent Number: 6,090,751
[45] Date of Patent: Jul. 18, 2000

[54] EMULSIFIABLE CONCENTRATE COMPRISING AN INSECTICIDAL 1-ARYLPYRAZOLE

[75] Inventor: Chiyu Roy Chen, Raleigh, N.C.

[73] Assignee: Rhone-Poulenc Agro, Lyons, France

[21] Appl. No.: 09/365,183

[22] Filed: Aug. 2, 1999

Related U.S. Application Data

[60] Provisional application No. 60/095,483, Aug. 5, 1998.
[51] Int. Cl.[7] .............................. A01N 3/02; A01N 43/40; A01N 43/48; A01N 43/56
[52] U.S. Cl. ......................... 504/116; 504/130; 504/139; 504/253; 504/254; 504/282
[58] Field of Search ..................................... 504/116, 130, 504/139, 253, 254, 282

[56] References Cited

U.S. PATENT DOCUMENTS 5,747,519  5/1998  Kodama et al. ..................... 514/407

*Primary Examiner*—Jose' G. Dees
*Assistant Examiner*—Alton Pryor
*Attorney, Agent, or Firm*—Burns, Doane, Swecker & Mathis, L.L.P.

[57] ABSTRACT

A new composition comprising an insecticidal 1-arylpyrazole, an N-alkylpyrrolidinone, a co-solvent and an emulsifier.

28 Claims, No Drawings

EMULSIFIABLE CONCENTRATE COMPRISING AN INSECTICIDAL 1-ARYLPYRAZOLE

This application claims the priority of copending U.S. Provisional Patent Application No. 60/095,483, filed Aug. 5, 1998, incorporated by reference herein in its entirety and relied upon.

The present invention relates to a new composition, particularly a new composition for use in crop protection, especially an emulsifiable concentrate comprising an insecticidal 1-arylpyrazole.

There exists a constant need to provide compositions for the efficient delivery of agrochemically active ingredients, e.g. insecticides, herbicides, fungicides and plant growth regulators. It is known in the art to mix the said active ingredients with adjuvants to deliver the said active ingredients more efficiently. One liquid mixture of active ingredients and adjuvants is called an emulsifiable concentrate (EC), said concentrate being emulsifiable in water. Very often, however, the properties of emulsifiable concentrates must be fine-tuned in ways unforseen to the skilled worker. It is generally unclear which ingredients should be combined to most efficiently deliver the active ingredient. An improperly formulated EC will allow the active ingredient to precipitate out in large crystals, the crystals being large enough to substantially inhibit efficient application of the diluted combination.

Among the prior art of emulsifiable concentrates, U.S. Pat. No. 5,071,463 teaches, inter alia, that in order to form stable aqueous emulsions from emulsifiable concentrates of substantially water-insoluble agriculturally active ingredients, the skilled worker should use a combination of the active ingredient, a hydrophobic solvent, e.g. an alkylpyrrolidinone, and another solvent having a Hansens solvent parameter description as follows: a) a dispersible component of from about 40% to 50%; b) a polar component of from about 25% to 40%; and c) an H-bonding component of from 10% to 30%. According to this prior art, examples of this type of solvent include $C_1$ to $C_4$ alkylpyrrolidinones, e.g., N-methylpyrrolidinone; a cyclic lactone, e.g., gamma-butyrolactone; and cyclic carbonates e.g., ethylene carbonate. This prior art reference also specifically teaches that the skilled worker should not use cyclohexanone in compositions to be used in forming stable aqueous emulsions.

PCT Patent Publication No. WO 97/22593 provides a description of an emulsifiable concentrate containing 5-amino-3-cyano-1-(2,6-dichloro-4-trifluoromethylphenyl)-4-ethylsulfinylpyrazole, N-octylpyrrolidinone, butyrolactone, Igepal CO630, and Rhodocal 70B.

It is an object of the present invention to provide a new composition for use in agrochemical applications.

Another object of the present invention is to provide a new composition for the formation of stable aqueous emulsions.

Another object of the present invention is to provide a new composition for the formation of stable aqueous emulsions of an insecticidal 1-arylpyrazole.

These and other objects are met in whole or in part by the present invention.

The present invention provides an agrochemically acceptable liquid composition, e.g. an emulsifiable concentrate, comprising an insecticidal 1-arylpyrazole; an N-alkylpyrrolidinone solvent; a co-solvent which is soluble, but not miscible, in water; and an emulsifier. The composition preferably comprises two emulsifiers.

Generally, the N-alkylpyrrolidinone solvent is a $(C_4–C_{12})$-N-alkylpyrrolidinone alkylpyrrolidinone solvent, preferably $(C_6–C_{10})$-N-alkylpyrrolidinone. A most highly preferred solvent is N-octylpyrrolidinone.

By the term "soluble in water" is meant having a solubility in water of from about 0.01 to about 30 percent by weight at 20° C. Preferably, the co-solvent is soluble in water from about 0.5 to about 10 percent by weight, most preferably from about 1 to about 3 percent by weight. Another property of the co-solvent is that water is soluble in the co-solvent, generally from about 0.1 to about 15 percent by weight, preferably from about 6 to about 12 percent by weight.

Generally, the co-solvent has from four to nine carbon atoms, preferably from 5 to 7 carbon atoms, most preferably 6 carbon atoms. The co-solvent is generally a ketone or an ester of a straight or branched-chain alcohol. The ketone is preferably a cyclic ketone, more preferably a cyclohexanone which is optionally substituted by one or two radicals selected from the group consisting of methyl, ethyl, chloro and fluoro. The ester is most preferably a methyl ester. Most preferably, the esters are Exxate® esters available from the Exxon Chemical Corporation and are described by P. Douglas Frisch in Standard Technical Publication 1328 of the American Society for Testing and Materials.

Preferably, the co-solvent has a dipole moment of from about 5 to about $12\mu$ (Debye), preferably from about 8.5 to about $10.5\mu$. In general, the measurement and values of dipole moments are described in the *Handbook of Solubility Parameters and Other Cohesion Parameters*, Allan F. M. Barton, CRC Press, 1983, Chapter 8 and other references therein. Another listing of dipole moments may also be found in the *Chemical Abstracts*.

A listing of co-solvent solubilities is provided in the *Encyclopedia of Chemical Technology*, Kirk-Othmer, fourth edition, John Wiley and Sons, 1995, Volume 14.

A list of preferred co-solvents includes:

| Solvent | $\mu$ (Debye) | Solubility at 20° C., weight % | |
|---|---|---|---|
| | | In water | Water in |
| cyclohexanone | 10.3 | 2.5 | 8.0 |
| methyl ethyl ketone | 9.2 | 26.8 | 11.8 |
| diisobutyl ketone | 8.9 | 0.05 | 0.75 |
| 2-heptanone | 8.6 | 0.43 | 1.45 |
| methyl isobutyl ketone | 9.0 | 1.6 | 1.9 |
| 3-pentanone | 9.4 | 3.4 | 2.6 |
| diisopropyl ketone | 9.1 | | |
| 3-hexanone | 9.6 | 1.57 | |
| 3-methyl-2-butanone | 9.2 | 6.53 | |
| acetophenone | 10.1 | 0.55 | 1.7 |
| 2-pentanone | 9.2 | 1.57 | |

Generally, the composition of the invention is substantially free of water. By the term "substantially free of water" is meant that the composition has less than about 7% by weight of water, preferably less than about 4% by water.

Suitable emulsifiers for use herein include one or more, preferably one or two, nonionic and/or anionic emulsifying agents. Examples of nonionic emulsifiers which may be mentioned include polyoxyethylenealkylphenyl ether, polyoxyethylenealkyl ether, polyethyleneglycol fatty ester, sorbitan fatty ester, polyoxyethylene sorbitan fatty ester, polyoxyethylenepolyoxypropylenealkyl ether, polyoxyethylene castor oil. Examples of anionic emulsifying agents which may be mentioned include alkyl sulfates, polyoxyethylenealkyl ether sulfates, sulfosuccinates, taurine derivatives, sarcosine derivatives, phosphoric esters, alkylbenzenesulfonates and the like.

The insecticidal 1-arylpyrazole is preferably a compound of formula (I):

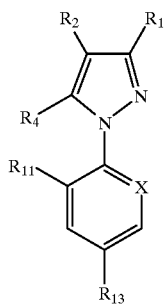

wherein:
R$_1$ is CN or methyl;
R$_2$ is S(O)$_n$R$_3$;
R$_3$ is alkyl or haloalkyl;
R$_4$ is hydrogen, halogen, —NR$_5$R$_6$, C(O)OR$_7$, —S(O)$_m$R$_7$, alkyl haloalkyl, —OR$_8$, or —N=C(R$_9$)(R$_{10}$); R$_4$ is preferably an amino group, which is unsubstituted or which is substituted by one or two substituents selected from the group consisting of alkyl, haloalkyl, —C(O)alkyl and alkoxycarbonyl;
each of R$_5$ and R$_6$ is, independently, hydrogen, alkyl, haloalkyl, —C(O)alkyl, alkoxycarbonyl or —S(O)$_r$CF$_3$; or R$_5$ and R$_6$ together form a divalent radical which is uninterrupted or interrupted by one or more heteroatoms which are O or S;
R$_7$ is alkyl or haloalkyl;
R$_8$ is alkyl, haloalkyl or hydrogen;
R$_9$ is hydrogen or alkyl;
R$_{10}$ is phenyl or heteroaryl, which is unsubstituted or is substituted by one or more hydroxy, halogen, —O-alkyl, —S-alkyl, cyano, or alkyl;
X is a nitrogen atom or a radical C—R$_{12}$;
each of R$_{11}$ and R$_{12}$ is, independently, halogen or hydrogen;
R$_{13}$ is halogen, haloalkyl, haloalkoxy, —S(O)$_q$CF$_3$, or —SF$_5$, preferably halogen, haloalkyl, haloalkoxy, or —SF$_5$;
each of m, n, q, and r is, independently, 0,1, or 2; provided that when R$_1$ is methyl, then R$_3$ is haloalkyl, R$_4$ is NH$_2$, R$_{11}$ is Cl, R$_{13}$ is CF$_3$, and X is N.

The alkyl and alkoxy groups of formula (I) are preferably lower alkyl and alkoxy groups, that is, radicals having one to four carbon atoms. The haloalkyl and haloalkoxy groups likewise preferably have one to four carbon atoms. The haloalkyl and haloalkoxy groups can bear one or more halogen atoms; preferred groups of this type include —CF$_3$ and —OCF$_3$.

The preparation of compounds of formula (I) can be effected according to processes described in International Patent Publications No. WO 87/03781, WO 93/06089 and WO 94/21606, as well as in European Patent Publications No. 0295117, 0403300, 0385809, and 0679650, German Patent Publication 19511269 and U.S. Pat. Nos. 5,232,940 and 5,236,938.

Preferably, the compound of formula (I) has one or more of the following features:
R$_1$ is CN;
R$_4$ is —NR$_5$R$_6$;
each of R$_5$ and R$_6$ is, independently, hydrogen, alkyl, haloalkyl, —C(O)alkyl, or alkoxycarbonyl;

X is C—R$_{12}$;
R$_{13}$ is halogen, haloalkyl, haloalkoxy, or —SF$_5$.

Most preferably, the compound of formula (I) is 5-amino-3-cyano-1-(2,6-dichloro-4-trifluoromethyl)phenyl-4-trifluoromethylsulfinylpyrazole, hereinafter known as Compound A; or 5-amino-3-cyano-1-(2,6-dichloro-4-trifluoromethylphenyl)-4-ethylsulfinylpyrazole, hereinafter known as Compound B.

The emulsifiers are generally known in the art as surfactants; these are described in the publications supra.

The composition of the invention generally comprises the insecticidal 1-arylpyrazole in an amount of from about 0.15 to about 0.8 kilogram of 1-arylpyrazole per liter of liquid, preferably from about 0.2 to about 0.4 kg/L. Generally, the 1-arylpyrazole is present in the composition in an amount of from about 5 percent by weight to about 60 percent by weight, preferably from about 10 percent to about 50 percent by weight.

The ratio of the alkylpyrrolidinone to the co-solvent is generally from about 7:1 to about 1:15, preferably from about 5:1 to about 1:12, depending on the particular insecticidal 1-arylpyrazole. The sum of the amount of alkylpyrrolidinone and co-solvent is generally from about 30% to about 80% of the weight of the composition, preferably from about 40% to about 70%.

The one or two emulsifiers are generally present in the composition in an amount of from about 5% to about 20% by weight.

The composition of the invention is most commonly used by diluting it in water. That is, the composition is generally added to a tank of water and diluted to provide a creamy emulsion that does not substantially break. Generally, about 1 part of the EC is added to from about 100 parts to about 10,000 parts of water, preferably from about 100 parts to about 1000 parts of water. Upon dilution, the composition of the invention, when in use, that is, diluted in water, provides minimal crystal growth and the crystals are small enough that they will not clog a 100 mesh filter (that is, having a pore size of about 149 microns), preferably a 325 mesh filter (that is, having a pore size of about 44 microns) when the diluted composition is passed through the filter. The diluted composition is generally stable. Generally, the composition when diluted possesses this property of limited crystal growth from 2 hours to 7 days from dilution, preferably from 4 hours to 3 days from dilution.

Most preferably, the composition of the invention may be added to water comprising a second agriculturally active ingredient. Alternatively, the second active ingredient may be added to the water after diluting the composition of the invention. Preferably, the second active ingredient is used in the treatment of cotton. It is preferably a pyrethroid insecticide or a chloronicotinyl insecticide.

The pyrethroid insecticide may be any insecticide of the well-known pyrethroid type. Examples of pyrethroid insecticides include the following:

1. allethrin[dl-3-allyl-2-methyl-4-oxo-2-cyclopentenyl-dl-cis, transchrysanthemate]
2. ethofenprox[2-(4-ethoxyphenyl)-2-methylpropyl-3-phenoxybenzyl ether]
3. cycloprothrin[(RS)-α-cyano-3-phenoxybenzyl(RS)-2,2-dichloro-1-(4-ethoxyphenyl)cyclopropane carboxylate]
4. cyhalothrin[(RS)-α-cyano-3-phenoxybenzyl(Z)-(1RS, 3RS) 3-(2-chloro-3,3,3-trifluoropropenyl)-2,2-dimethylcyclopropanecarboxylate]
5. cyfluthrin[(RS)-α-cyano-4-fluoro-3-phenoxybenzyl (1RS, 3RS)-(1RS, 3RS)-3-(2,2-dichlorovinyl)-2,2-dimethylcyclopropanecarboxylate]

6. cypermethrin[(RS)-α-cyano-3-phenoxybenzyl(1RS, 3RS)-(1RS, 3SR)-3-(2,2-dichlorovinyl)-2,2-dimethylcyclopropanecarboxylate]
7. pyrethrin
8. tralomethrin[(S)-α-cyano-3-phenoxybenzyl(1R, 3S)-2,2-dimethyl-3-(1,2,2,2-tetrabromoethyl)-cyclopropanecarboxylate]
9. fenvalerate[(RS)-α-cyano-3-phenoxybenzyl(RS)-2-(4-chlorophenyl)-3-methylbutanoate]
10. fenpropathrin[(RS)-α-cyano-3-phenoxybenzyl-2,2,3,3-tetramethylcyclopropanecarboxylate]
11. flucythrinate[(RS)-α-cyano-3-phenoxybenzyl-(S)-2-(4-difluoromethoxyphenyl)-3-methylbutylate]
12. permethrin[3-phenoxybenzyl(1RS, 3RS)-1RS, 3RS)-(2,2-dichlorovinyl)-2,2-dimethylcyclopropanecarboxylate]
13. bifenthrin[2-methylbiphenyl-3-yl-methyl(Z)-(IRS, 3RS)-3-(2-chloro-3,3,3-trifluoroprop-1-enyl)-2,2-dimethylcyclopropanecarboxylate]
14. silafluofen[4-ethoxyphenyl-[3-(3-phenoxy-4-fluorophenyl)propyl](dimethyl)silane]
15. resmethrin[5-benzyl-3-furylmethyl dl-cis, transchrysanthemate]
16. tefluthrin[2,3,5,6-tetrafluoro-4-methylbenzyl-(1RS)-cis-3-(Z-2-chloro-3,3,3-trifluoroprop-1-enyl)-2,2-dimethylcyclopropanecarboxylate]
17. acrinathrin[(S)-α-cyano-3-phenoxybenzyl(Z)-(1R, 3S)-2,2-dimethyl-3-[2-(2,2,2-trifluoro-1-trifluoromethylethoxycarbonyl)vinyl] cyclopropanecarboxylate]
18. prarethrin[(RS)-2-methyl-4-oxo-3-prop-2-enylcyclopent-2-enyl(1RS)-cis, trans-2,2-dimethyl-3-(2-methylprop-1-enyl)cyclopropanecarboxylate]
19. cismethrin[5-benzyl-3-furylmethyl(1R)-trans-2,2-dimethyl-3-(2-methylprop-1-enyl) cyclopropanecarboxylate]
20. d-phenothrin[3-phenoxybenzyl(1RS)-cis,trans-2,2-dimethyl-3-(2-methylprop-1-enyl) cyclopropanecarboxylate]
21. deltamethrin[(S)-α-cyano-3-phenoxybenzyl(1R)-cis-3-(2,2-dibromovinyl)-2,2-dimethylcyclopropanecarboxylate]
22. tetramethrin[cyclohex-1-ene-1,2-dicarboximidomethyl-(1RS, 3RS, 1RS, 3SR)-2,2-dimethyl-3-(2-methylprop-1-enyl) cyclopropanecarboxylate]
23. fluvalinate[(RS)α-cyano-3-phenoxybenzyl N-(2-chloro-α,α,α-trifluoro-p-tolyl)-DL-valinate].

The chloronicotinyl insecticides are likewise known to those of skill in the art. Nicotinyl insecticides are commonly known as agonists or antagonists of acetylcholine receptors.

Examples of agonists and antagonists of the nicotinergic acetylcholine receptors are those disclosed in European Patent Publication Nos. 0464830, 0428941, 0425978, 0386565, 0383091, 0375907, 0364844, 0315826, 0259738, 0254859, 0235725, 0212600, 0192060, 0163855, 0154178, 0136686, 0303570, 0302833, 0306696, 0189972, 0455000, 0135956, 0471372, and 0302389; German Published Application Nos. 3639877, 3712307; Japanese Application Nos. 03/220,176; 02/207,083; 63/307,857; 63/287,764; 03/246,283; 03/279,359; and 03/255,072; U.S. Pat. Nos. 5,034,524; 4,948,798; 4,918,086; 5,039,686; and 5,034,404; PCT Publication Nos. WO 91/17659 and 91/4965; French Published Application No. 2611114; and Brazilian Application No. 88 03 621.

These compounds are described as a group having the name nitromethylenes and related compounds. These compounds may preferably be described by the general structure (II):

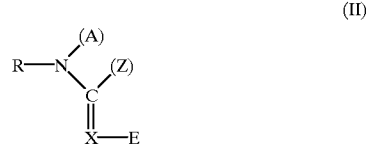

wherein:
R is hydrogen, optionally substituted acyl, alkyl, aryl, aralkyl, heteroaryl, or heteroarylalkyl;
A is a monofunctional group selected from H, acyl, alkyl, aryl, or bifunctional groups attached to the Z remainder;
E is an electron-attracting remainder;
X is the remainder —CH= or =N— where the —CH= remainder instead of an H atom can be attached to the Z remainder;
Z is a monofunctional group selected from alkyl, —OR, —SR,

or bifunctional groups which are attached to the A remainder or to the X remainder.

Preferably, the compounds of Formula II have the following substitutions:
R is H or optionally substituted remainders selected from acyl, alkyl, aryl, aralkyl, heteroaryl or heteroarylalkyl.
Suitable acyl remainders include formyl, alkylcarbonyl, arylcarbonyl, alkylsulfonyl, arylsulfonyl, and (alkyl-)-(aryl-)-phosphoryl, which in turn can be substituted. Suitable alkyls are $C_1$–$C_{10}$ alkyl, in particular $C_1$–$C_4$ alkyl, specifically methyl, alkyl, i-propyl, sec.- or t-butyl, which in turn can be substituted. Suitable aryls include phenyl and naphthyl, most preferably, phenyl. Suitable aralkyls include phenylmethyl and phenethyl. Suitable heteroaryls include heteroaryls having up to 10 ring atoms and N, O, S, in particular, N, as the hetero atoms. Examples include thiophenyl, furyl, thiazolyl, imidazolyl, pyridyl, and benzthiazolyl. Suitable heteroarylalkyls include heteroarylmethyl, heteroarylethyl having up to 6 ring atoms and N, O, S, in particular, N, as hetero atoms.

Preferably, the alkyl groups have between 1 and 4, more preferably between 1 and 2, carbon atoms, such as methyl, ethyl, n- and i-propyl and n-, i- and t-butyl. Alkoxy groups preferably have been 1 and 4, more preferably between 1 and 2, carbon atoms, such as methoxy, ethoxy, n- and i-propyloxy, and n-, i- and t-butyloxy. Alkylthios preferably have between 1 and 4, more preferably between 1 and 2, carbon atoms, such as methylthio, ethylthio, n- and i-propylthio and n-, i- and t-butylthio. Haloalkyls preferably have between 1 and 4, more preferably between 1 and 2, carbon atoms, and preferably between 1 and 5, more preferably between 1 and 3, halogen atoms, wherein the halogen atoms are the same or different, and preferably are fluorine, chlorine, or bromine, more preferably fluorine. An example of a preferred haloalkyl group is trifluoromethyl.

Suitable optional substituents include hydroxy; halo, preferably fluoro, chloro, or bromo, cyano; nitro; amino;

monoalkyl and dialkylaminos preferably having between 1 and 4, more preferably between 1 and 2, carbon atoms per alkyl group, for example, methylamino, ethylamino, n- and i- propylamino and methyl-n-butylamino; carboxyls; carbalkoxys preferably having between 2 and 4, more preferably between 2 and 3, carbon atoms, such as carbomethoxy and carboethoxy; sulfo (—SO₃H); alkylsulfonyl, preferably having between 1 and 4, more preferably between 1 and 2, carbon atoms, such as methylsulfonyl and ethylsulfonyl; arylsulfonyl preferably having 6 or 10 aryl carbon atoms, such as phenylsulfonyl, and heteroarylamino and heteroarylalkylamino such as chloropyridylamino and chloropyridylmethylamino.

A is H or optionally substituted remainders selected from acyl, alkyl, or aryl, which preferably have the meanings stated above. A also stands for a bifunctional group. Typical examples are optionally substituted alkylene groups having between 1 and 4, more preferably between 1 and 2, carbon atoms.

A and Z, together with the atoms to which they are bonded, may form a saturated or unsaturated heterocyclic ring. The heterocyclic ring may contain one or two identical or different hetero atoms and/or hetero groups. Preferable hetero atoms are oxygen, sulfur, or nitrogen; typical hetero groups are N-alkyl, where the alkyl of the N-alkyl group preferably contains between 1 and 4, more preferably between 1 and 2, carbon atoms. Typical alkyls are methyl, ethyl, n- and i-propyl and n-, i- and t-butyl. The heterocyclic ring contains between 5 and 7, preferably five or six, ring members. Examples of suitable heterocyclic rings include pyrrolidine, piperidine, piperazine, hexamethylenimine, morpholine, and N-methylpiperazine.

E is an electron-attracting remainder, in particular NO₂, CN, haloalkyl carbonyl as well as 1,5-halogen-C₁-C₄-carbonyl, in particular C(O)CF₃.

X is —CH= or —N=.

Z is an optionally substituted remainder selected from alkyl, —OR, —SR, or —NRR, wherein R and the substituents have the meaning stated above.

Z can form a saturated or unsaturated heterocyclic ring at the position of X together with the atom to which it is attached and the remainder

The heterocyclic ring can contain an additional one or two identical or different hetero atoms and/or hetero groups. The hetero atoms are preferably oxygen, sulfur, or nitrogen, and the hetero groups are N-alkyl, where the alkyl or N-alkyl group preferably contains between 1 and 4, more preferably between 1 and 2, carbon atoms. Preferred alkyls are methyl, ethyl, n- and i-propyl, and n-, i-, and t-butyl. The heterocyclic ring contains between 5 and 7, preferably between 5 and 6, ring members. Suitable examples of heterocyclic rings include pyrrolidine, piperidine, piperazine, hexamethylenediamine, morpholine, and N-methylpiperazine.

The agonists and antagonists of the nicotinergic acetylcholine receptors are preferably compounds having the following structure:

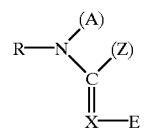

wherein:

R is 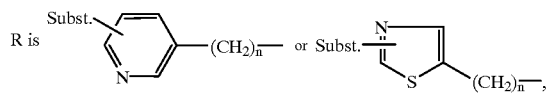

n is 1 or 2,

Subst. stands for one of the substituents listed above, preferably, halogen, more preferably, chlorine, and A, Z, X, and E have the meanings stated above.

Specifically, the following compounds are cited:

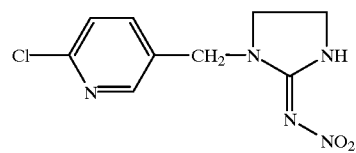

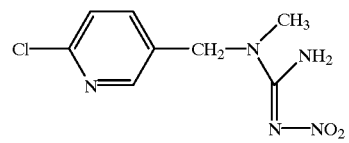

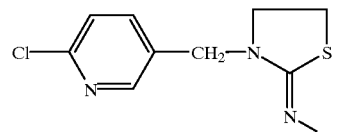

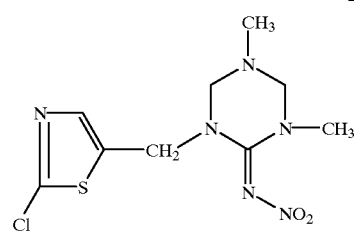

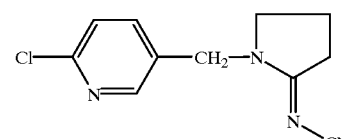

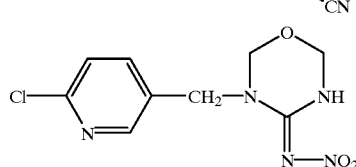

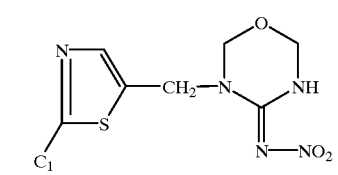

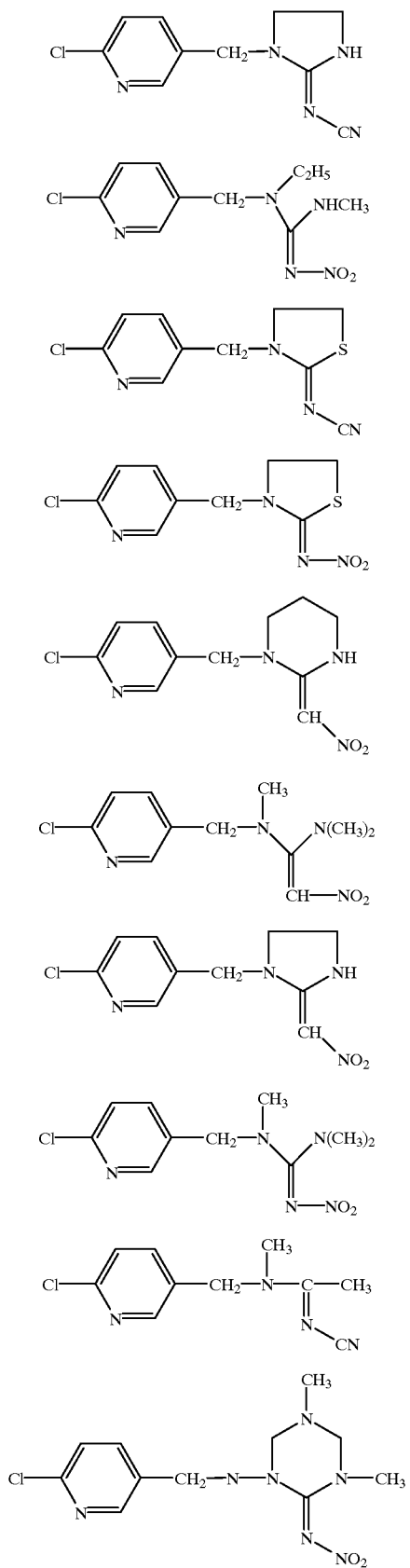
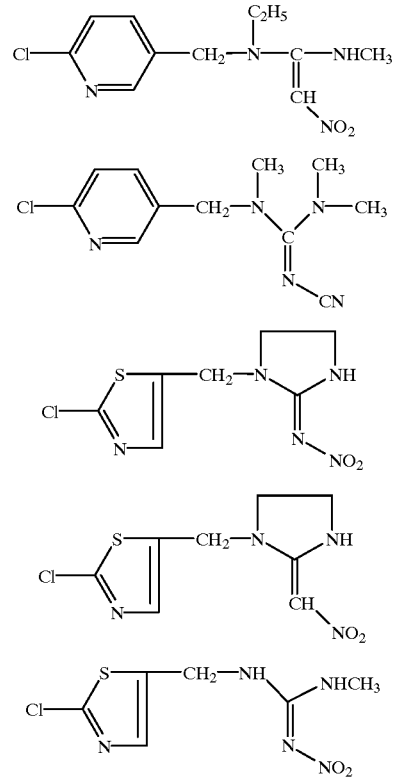
Especially preferred agonists and antagonists of the nicotinergic acetylcholine receptors are compounds having the structures:
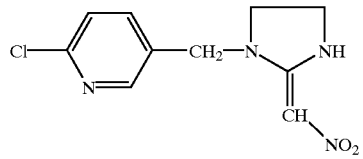
(IIa)
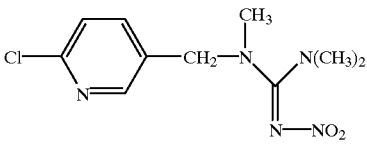
(IIb)
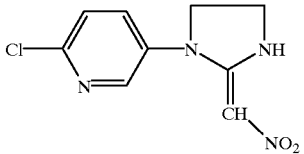
(IIc)
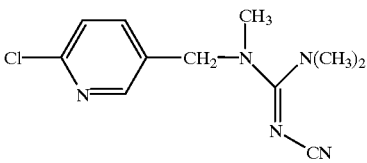
(IId)

-continued

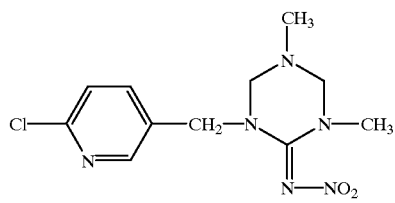

(IIe)

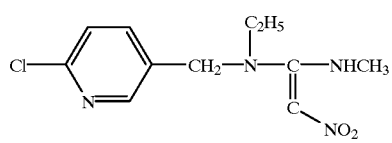

(IIf)

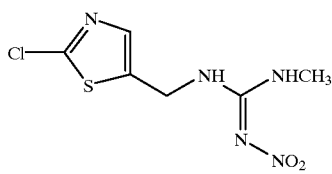

(IIg)

in particular compounds having the structure

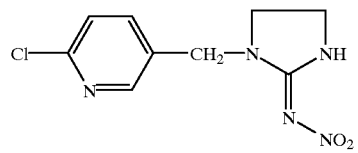

(IIi)

The most preferred compounds in this class are imidacloprid and thiomethoxam.

The following Examples provide non-limiting illustrations of the invention.

EXAMPLE 1

An EC is prepared according to the following proportions:

| Ingredient | % by weight |
|---|---|
| Compound A | 28.29 |
| N-octylpyrrolidinone | 47.84 |
| Cyclohexanone | 10.00 |
| Antarox 724P (non-ionic surfactant) | 6.00 |
| Rhodacal 60 BHF (anionic surfactant) | 4.00 |
| Water | 3.86 |

When poured into water at typical concentrations that are applied in typical agricultural settings, the emulsion thus formed was acceptable and provided minimal crystal growth compared to the formulations suggested by the prior art.

EXAMPLE 2

An acceptable EC is prepared according to the following proportions:

| Ingredient | % by weight |
|---|---|
| Compound B | 10.00 |
| N-octylpyrrolidinone | 5.00 |
| Cyclohexanone | 55.00 |
| N-methylpyrrolidnone | 5.00 |
| Tristyrylphenol surfactant | 10.00 |
| Emulsified methyl ester | 15.00 |

EXAMPLE 3

The experiment of Example 1 is repeated according to the following proportions to provide an acceptable EC:

| Ingredient | % by weight |
|---|---|
| Compound A | 27.15 |
| N-octylpyrrolidinone | 49.15 |
| Exxate 700 | 10 |
| (Soprophor BSU) Tristyrylphenol surfactant | 5 |
| Soprophor 4D384 (Tristyrylphenol surfactant) | 5 |
| Water | 3.70 |

While the invention has been described in terms of various preferred embodiments, the person skilled in the art will appreciate that various modifications, substitutions, omissions and changes can be made without departing from the spirit thereof. Accordingly, it is intended that the scope of the present invention be limited solely by the scope of the following claims, including equivalents thereof.

What is claimed is:

1. An agrochemically acceptable liquid composition comprising: (a) an insecticidally effective amount of insecticidal 1-arylpyrazole; (b) an N-alkylpyrrolidinone solvent; (c) a co-solvent which has a solubility in water of from about 0.01 percent by weight to about 30 percent by weight at 20° C.; and (d) an emulsifier; wherein the ratio of said N-alkylpyrrolidinone to said co-solvent is from about 7:1 to about 1:15, said composition comprising sufficient amounts of (b), (c) and (d) to prevent precipitation of large crystals of the 1-arylpyrazole following dilution of the composition with water.

2. A composition according to claim 1, comprising two emulsifiers.

3. A composition according to claim 1, wherein the co-solvent has from four to nine carbon atoms.

4. A composition according to claim 3, wherein the co-solvent is cyclohexanone, methyl ethyl ketone, diisobutylketone, 2-heptanone, methyl isobutyl ketone, 3-pentanone, diisopropyl ketone, 3-hexanone, 3-methyl-2-butanone, acetophenone or 2-pentanone.

5. A composition according to claim 1, wherein the co-solvent has a dipole moment of from 5 to $12\mu$.

6. A composition according to claim 1, wherein water is soluble in the co-solvent from about 0.1 to about 15 percent by weight.

7. A composition according to claim 1, which is substantially free of water.

8. A composition according to claim 1, wherein the N-alkylpyrrolidinone solvent comprises a $(C_6-C_{12})$-N-alkylpyrrolidinone.

9. A composition according to claim 8, wherein the ($C_6$–$C_{12}$)-N-alkylpyrrolidinone is N-octylpyrrolidinone.

10. A composition according to claim 1, wherein the insecticidal 1-arylpyrazole is a compound having the formula:

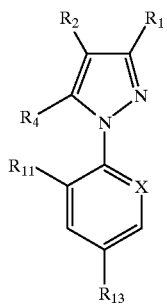

wherein:
$R_1$ is CN or methyl;
$R_2$ is $S(O)_n R_3$;
$R_3$ is alkyl or haloalkyl;
$R_4$ is hydrogen, halogen, —$NR_5 R_6$, $C(O)OR_7$, —$S(O)_m R_7$, alkyl, haloalkyl, —$OR_8$, or —$N=C(R_9)(R_{10})$;
each of $R_5$ and $R_6$ is, independently, hydrogen, alkyl, haloalkyl, —C(O)alkyl, alkoxycarbonyl or —$S(O)_r CF_3$; or $R_5$ and $R_6$ together form a divalent radical which is uninterrupted or interrupted by one or more heteroatoms which are O or S;
$R_7$ is alkyl or haloalkyl;
$R_8$ is alkyl, haloalkyl or hydrogen;
$R_9$ is hydrogen or alkyl;
$R_{10}$ is phenyl or heteroaryl, which is unsubstituted or is substituted by one or more hydroxy, halogen, —O-alkyl, —S-alkyl, cyano, or alkyl;
X is a nitrogen atom or a radical C—$R_{12}$;
each of $R_{11}$ and $R_{12}$ is, independently, halogen or hydrogen;
$R_{13}$ is halogen, haloalkyl, haloalkoxy, —$S(O)_q CF_3$, or —$SF_5$;
each of m, n, q, and r is, independently, 0,1, or 2;
provided that when $R_1$ is methyl, then $R_3$ is haloalkyl, $R_4$ is $NH_2$, $R_{11}$ is Cl, $R_{13}$ is $CF_3$, and X is N.

11. A composition according to claim 10, wherein $R_4$ is —$NR_5 R_6$ wherein each of $R_5$ and $R_6$ is, independently, hydrogen, alkyl, haloalkyl, —C(O)alkyl or alkoxycarbonyl.

12. A composition according to claim 10, wherein $R_{13}$ is halogen, haloalkyl, haloalkoxy or —$SF_5$.

13. A composition according to claim 11, wherein $R_{13}$ is halogen, haloalkyl, haloalkoxy or —$SF_5$.

14. The composition according to claim 10, wherein the compound of formula (I) has one or more of the following features:
$R_1$ is CN;
$R_4$ is —$NR_5 R_6$;
each of $R_5$ and $R_6$ is, independently, hydrogen, alkyl, haloalkyl, —C(O)alkyl, or alkoxycarbonyl;
X is C—$R_{12}$;
$R_{13}$ is halogen, haloalkyl, haloalkoxy, or —$SF_5$.

15. A composition according to claim 10, wherein the compound of formula (I) is 5-amino-3-cyano-1-(2,6-dichloro-4-trifluoromethyl)phenyl-4-trifluoromethylsulfinylpyrazole or 5-amino-3-cyano-1-(2,6-dichloro-4-trifluoromethylphenyl)-4-ethylsulfinylpyrazole.

16. The composition according to claim 1, comprising the 1-arylpyrazole in an amount of from about 0.15 to about 0.8 kilogram per liter of liquid.

17. A composition according to claim 16, comprising the 1-arylpyrazole in an amount of from about 0.2 to about 0.4 kilogram per liter of liquid.

18. A composition according to claim 1, which when diluted in water does not provide crystals which will clog an approximately 149 micron filter when the diluted material is passed through the filter.

19. A composition according to claim 18, which when diluted in water does not provide crystals which will clog an approximately 44 micron filter when the diluted material is passed through the filter.

20. A composition according to claim 18, comprising a second agriculturally active ingredient in the water.

21. A composition according to claim 18, wherein when diluted a second active ingredient is added after diluting the composition.

22. A composition according to claim 20, wherein the second active ingredient is an active agent used in the treatment of cotton.

23. A composition according to claim 21, wherein the second active ingredient is an active agent used in the treatment of cotton.

24. A composition according to claim 20, wherein the second active ingredient is a pyrethroid insecticide or a chloronicontinyl insecticide.

25. A composition according to claim 21, wherein the second active ingredient is a pyrethroid insecticide or a chloronicotinyl insecticide.

26. A composition according to claim 22, wherein the second active ingredient is a pyrethroid insecticide or a chloronicotinyl insecticide.

27. A composition according to claim 1, wherein the sum of the amount of alkylpyrrolidinone and co-solvent is about 30% to about 80% of the weight of the composition.

28. An agrochemically acceptable liquid composition comprising: (a) an insecticidally effective amount of insecticidal 1-arylpyrazole; (b) an N-alkylpyrrolidinone solvent; (c) a co-solvent which has a solubility in water of from about 0.01 percent by weight to about 30 percent by weight at 20° C.; (d) an emulsifier; and (e) a chloronicotinyl insecticide; said composition comprising sufficient amounts of (b), (c) and (d) to prevent precipitation of large crystals of the 1-arylpyrazole following dilution of the composition with water.

* * * * *

UNITED STATES PATENT AND TRADEMARK OFFICE
CERTIFICATE OF CORRECTION

PATENT NO.   : 6,090,751
DATED        : July 18, 2000
INVENTOR(S)  : Chiyu Roy Chen It is certified that error appears in the above-identified patent and that said Letters Patent is hereby corrected as shown below:

Title page,
Item [56], References Cited, please add the following prior art documents:

| | | | | | |
|---|---|---|---|---|---|
| -- | 5,236,938 | 08/93 | Huang et al | 514 | 341 |
| | 5,232,940 | 08/93 | Hatton et al | 514 | 407 |
| | 5,071,463 | 12/91 | Narayanan et al | 71 | 79 |
| | 5,063,236 | 11/91 | Gsell | 514 | 318 |
| | 5,049,571 | 09/91 | Gsell | 514 | 345 |
| | 5,039,686 | 08/91 | Davies et al | 514 | 341 |
| | 5,034,524 | 07/91 | Shiokawa et al | 544 | 124 |
| | 5,034,404 | 07/91 | Uneme et al | 514 | 365 |
| | 4,963,574 | 10/90 | Bachmann et al | 514 | 357 |
| | 4,963,572 | 10/90 | Gsell | 514 | 357 |
| | 4,948,798 | 08/90 | Gsell | 514 | 275 |
| | 4,918,088 | 04/90 | Gsell | 514 | 357 |
| | 4,918,086 | 04/90 | Gsell | 514 | 351 |
| | 4,914,113 | 04/90 | Shiokawa et al | 514 | 333 |
| | 4,849,432 | 07/89 | Shiokawa et al | 514 | 341 |
| | 4,812,454 | 03/89 | Shiokawa et al | 514 | 256 |
| | 4,806,553 | 02/89 | Shiokawa et al | 514 | 332 |
| | 4,803,277 | 02/89 | Shiokawa et al | 546 | 264 |
| | 4,774,247 | 09/88 | Shiokawa et al | 514 | 256 |
| | 4,772,620 | 09/88 | Shiokawa et al | 514 | 341 |
| | 4,742,060 | 05/88 | Shiokawa et al | 514 | 252 |
| | 4,647,570 | 03/87 | Shiokawa et al | 514 | 341 |
| | 97/22593 | 06/97 | WO | | |
| | 94/21606 | 09/94 | WO | | |
| | 93/06089 | 04/93 | WO | | |
| | 91/04965 | 04/91 | WO | | |
| | 91/17659 | 11/91 | WO | | |
| | 87/03781 | 07/87 | WO | | |
| | 63-307857 | 06/87 | JP | | |
| | 63-287764 | 05/87 | JP | | |
| | 03-255072 | 05/90 | JP | | |
| | 03-279359 | 03/90 | JP | | |
| | 03-246283 | 02/90 | JP | | |

UNITED STATES PATENT AND TRADEMARK OFFICE
CERTIFICATE OF CORRECTION

PATENT NO. : 6,090,751
DATED : July 18, 2000
INVENTOR(S) : Chiyu Roy Chen

It is certified that error appears in the above-identified patent and that said Letters Patent is hereby corrected as shown below:

References Cited, cont'd.

| | | |
|---|---|---|
| 03-220176 | 01/90 | JP |
| 02/207083 | 02/89 | JP |
| 19511269 | 10/95 | DE |
| 3712307 | 10/88 | DE |
| 3639877 | 05/88 | DE |
| 0679650 | 11/95 | EP |
| 0471372 | 02/92 | EP |
| 0464830 | 01/92 | EP |
| 0455000 | 11/91 | EP |
| 0428941 | 05/91 | EP |
| 0425978 | 05/91 | EP |
| 0403300 | 12/90 | EP |
| 0386565 | 09/90 | EP |
| 0385809 | 09/90 | EP |
| 0383091 | 08/90 | EP |
| 0375907 | 07/90 | EP |
| 0364844 | 04/90 | EP |
| 0163855 | 06/89 | EP |
| 0315826 | 05/89 | EP |
| 0306696 | 03/89 | EP |
| 0303570 | 02/89 | EP |
| 0302833 | 02/89 | EP |
| 0302389 | 02/89 | EP |
| 0295117 | 12/88 | EP |
| 0259738 | 03/88 | EP |
| 0254859 | 02/88 | EP |
| 0154178 | 10/87 | EP |
| 0235725 | 09/87 | EP |
| 0212600 | 03/87 | EP |
| 0192060 | 08/86 | EP |
| 0189972 | 08/86 | EP |
| 0135956 | 04/85 | EP |

UNITED STATES PATENT AND TRADEMARK OFFICE
CERTIFICATE OF CORRECTION

PATENT NO. : 6,090,751
DATED : July 18, 2000
INVENTOR(S) : Chiyu Roy Chen

It is certified that error appears in the above-identified patent and that said Letters Patent is hereby corrected as shown below:

References Cited, cont'd.

Derwent WPI Acc No. 89-093657 (1989), abstract of BR 8803621 and patent family list.
Derwent WPI Acc No. 88-252222 (1988), abstract of FR 2611114 and patent family list.

Signed and Sealed this

Tenth Day of September, 2002

*Attest:*

JAMES E. ROGAN
*Director of the United States Patent and Trademark Office*

*Attesting Officer*